United States Patent [19]

Deighan et al.

[11] Patent Number: 5,715,812
[45] Date of Patent: *Feb. 10, 1998

[54] COMPLIANCE METER FOR RESPIRATORY THERAPY

[75] Inventors: Joseph Deighan, Gardner; Steven L. Phillips; Linn D. Wanbaugh, both of Olathe, all of Kans.; Philip M. Metzler, St. Charles, Mo.

[73] Assignee: Nellcor Puritan Bennett, Pleasanton, Calif.

[*] Notice: The term of this patent shall not extend beyond the expiration date of Pat. No. 5,517,983.

[21] Appl. No.: 615,498

[22] Filed: Mar. 12, 1996

Related U.S. Application Data

[63] Continuation of Ser. No. 987,643, Dec. 9, 1992, Pat. No. 5,517,983.

[51] Int. Cl.$^6$ .................................................. A61M 16/00
[52] U.S. Cl. ........................... 128/204.23; 128/204.21; 128/205.23
[58] Field of Search ........................ 128/204.21, 204.23, 128/205.23, 202.22

[56] References Cited

U.S. PATENT DOCUMENTS

| | | | |
|---|---|---|---|
| H1039 | 4/1992 | Tripp, Jr. et al. | 128/202.16 |
| 3,595,228 | 7/1971 | Simon et al. | 128/202.22 |
| 3,730,173 | 5/1973 | Deaton | 128/720 |
| 3,942,513 | 3/1976 | Frank | 126/721 |
| 4,155,357 | 5/1979 | Dahl | 128/202.22 |
| 4,178,932 | 12/1979 | Ryder et al. | 604/318 |
| 4,220,142 | 9/1980 | Rosen et al. | 128/848 |
| 4,316,182 | 2/1982 | Hodgson | 128/202.22 |
| 4,361,107 | 11/1982 | Gereg | 116/266 |
| 4,474,175 | 10/1984 | Hudimac, Jr. | 128/202.22 |
| 4,655,213 | 4/1987 | Rapoport et al. | 128/205.25 |
| 4,658,832 | 4/1987 | Brugnoli | 128/719 |
| 4,766,894 | 8/1988 | Legrand et al. | 128/202.22 |
| 4,803,471 | 2/1989 | Rowland | 128/202.22 |
| 4,825,802 | 5/1989 | Le Bec | 128/202.22 |
| 4,984,158 | 1/1991 | Hillsman | 128/200.23 |
| 5,020,527 | 6/1991 | Dessertine | 128/200.14 |
| 5,097,424 | 3/1992 | Ginerri et al. | 128/204.23 |
| 5,148,802 | 9/1992 | Sanders et al. | 128/204.18 |
| 5,199,424 | 4/1993 | Sullivan et al. | 128/204.18 |
| 5,203,343 | 4/1993 | Axe et al. | 128/725 |
| 5,233,987 | 8/1993 | Fabian et al. | 607/41 |
| 5,320,092 | 6/1994 | Ryder | 128/202.22 |
| 5,517,983 | 5/1996 | Deighan et al. | 128/204.23 |
| 5,537,997 | 7/1996 | Melchenburg et al. | 128/205.23 |
| 5,540,219 | 7/1996 | Mechlenburg et al. | 128/205.23 |
| 5,560,351 | 10/1996 | Gravenstein et al. | 128/205.23 |

FOREIGN PATENT DOCUMENTS

| | | |
|---|---|---|
| 0 656 216 A2 | 7/1995 | European Pat. Off. . |
| 9217231 | 10/1992 | WIPO ............... 128/200.23 |

OTHER PUBLICATIONS

J. Krieger, et al. Eur. Respir J (1988), pp. 1:436–438, "Objective Measurement of Compliance with Nasal CPAP Treatment for Obstructive Sleep Apnea Syndrome".

M. K. Reeves Hoche, et al., American Review of Respiratory Disease (1990), vvol. 141; p. A862 "An Objective Trial of Nasal Continuous Positive Airway Pressure Treatment Compliance".

R. Idatna, American Review of Respiratory Disease (1990), vol. 141: p. A863, "A Multicentric Survey of Long Term Compliance with Nasal CPAP Treatment in Patients with Obstructive Sleep Apnea Syndrome".

Kribbs, et al., Brian Information Service/Brian Research Institute University of California, Los Angeles, Sleep Research vol. 20 (1991), p. 270 "Objective Monitoring of Nasal CPAP Usage Patterns in OSAS Patients".

*Primary Examiner*—Aaron J. Lewis
*Attorney, Agent, or Firm*—Fulwider Patton Lee & Utecht, LLP

[57] ABSTRACT

A respiratory apparatus (10) operable for delivering a breathable gas to the airway of a patient includes a status monitor (24,26) for determining the status of usage of the unit by the patient and a timer (32) for determining the accumulated time of usage of the unit by the patient.

4 Claims, 1 Drawing Sheet

5,715,812

COMPLIANCE METER FOR RESPIRATORY THERAPY

This is a continuation of application Ser. No. 07/987,643, filed Dec. 9, 1992, now U.S. Pat. No. 5,517,983.

BACKGROUND OF THE INVENTION

1. Field of the Invention

The present invention relates to the field of respiratory therapy. More particularly, the invention concerns a respiratory apparatus operable for delivering a breathable gas to the airway of a patient and includes a status monitor for determining the status of usage of the unit by the patient and a timer for determining the accumulated time of usage of the unit by the patient.

2. Description of the Prior Art

In the treatment of obstructive sleep apnea, for example, it has been found that the application of pressurized ambient air to the nasal passages of a patient provides a pneumatic splint that maintains the patency of the airway. This type of respiratory therapy can be implemented by a home therapy device having a blower unit, a nasal mask, and a pneumatic hose interconnecting the two. When the patient is ready to retire for the night, the mask is placed in position over the patient's nose and the blower activated to deliver the prescribed therapeutic pressure regimen to the patient's airway. The prescribed therapy may include continuous positive air pressure (CPAP), intermittent positive air pressure (IPAP), or a variety of other pressure regimens, depending upon the needs of the patient.

As those skilled in the art appreciate, the effectiveness of an apnea therapy device depends upon its usage. In order to determine usage, some prior art devices have incorporated a timer which indicates accumulated operational time of the device. Such prior art devices, however, do not determine whether the device has actually been used by the patient. Even though the therapy device has been turned on, the patient may not have used the device or the nasal mask may have become dislodged during the sleep session.

SUMMARY OF THE INVENTION

The present invention solves the prior art problems discussed above and provides a distinct advance in the state of the art. More particularly, the present invention determines the accumulated time of actual usage of a respiratory apparatus.

The preferred respiratory apparatus includes a gas delivery unit operable for coupling with the airway of a patient in delivering a breathable gas thereto, a status monitor for monitoring a parameter indicative of the status of usage of the delivery unit, and a timer responsive to the status monitor for determining the accumulated time of usage of the delivery unit by the patient. In one embodiment of the invention, the status monitor includes a pressure sensor for sensing the pressure at the nasal mask and the timer includes an hour meter. When the sensed nasal pressure exceeds a predetermined level indicating that the mask is in place about the patient's nose, the hour meter is activated to register accumulated usage time.

DETAILED DESCRIPTION OF THE PREFERRED EMBODIMENT

Figure 1:
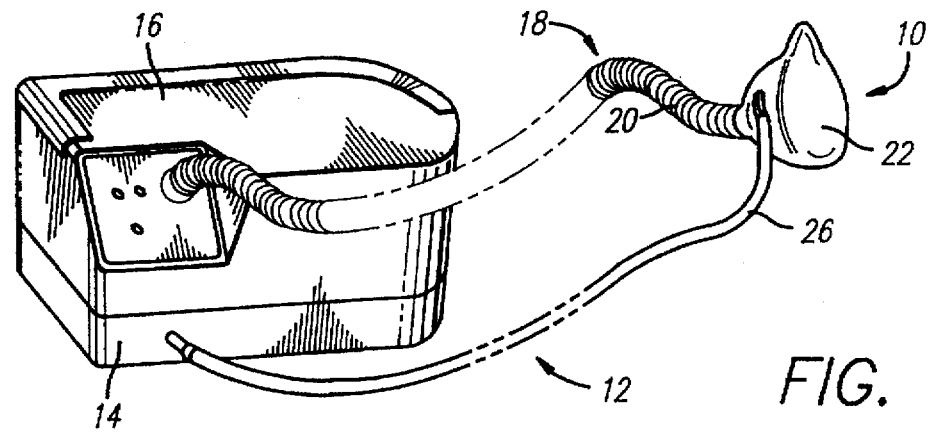
FIG. 1 is a schematic representation of the preferred respiratory apparatus.

Referring initially to FIG. 1, preferred respiratory apparatus 10 includes gas delivery unit 12, and compliance circuit 14. Gas delivery unit 12 includes pressure supply device 16 and patient connector 18. Pressure supply device is preferably a conventional respiratory therapy device operable for delivering ambient air at a selected pressure such as the COMPANION 318 nasal CPAP system available from Puritan-Bennett of Lenexa, Kans. The preferred patient connector 18 is known as an ADAM circuit also available from Puritan-Bennett and further includes connection hose 20 and nasal mask 22.

Figure 2:
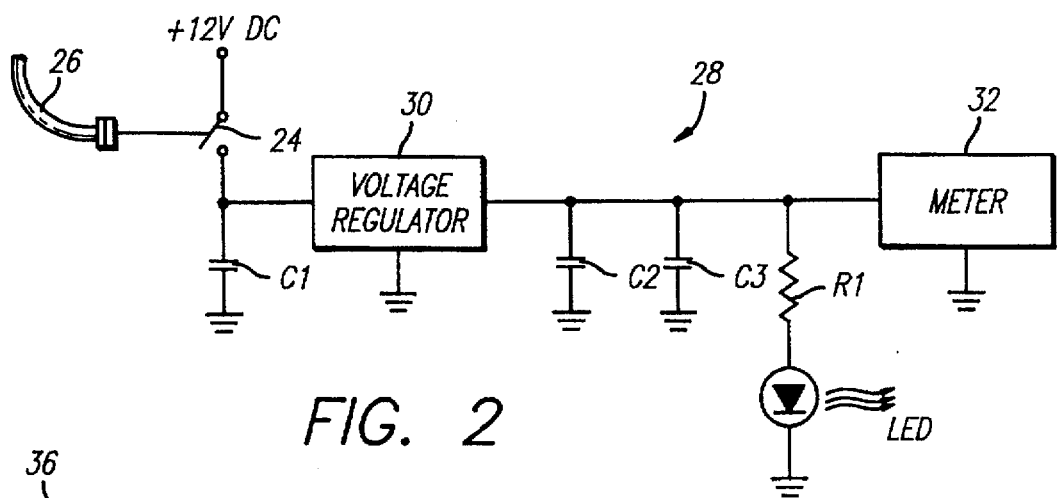
FIG. 2 is an electrical schematic diagram of the compliance circuit of FIG. 1.

FIG. 2 illustrates compliance circuit 14, which includes adjustable pressure switch 24 (P/N MPL-500-P-G-40 available from Micro Pneumatic Logic Co.), hose 26 pneumatically interconnecting mask 22 and switch 24, and timer circuit 28. Circuit 28 includes capacitor C1 (0.1 uF), voltage regulator 30 (type 7508), capacitor C2 (0.1 uF), capacitor C3 (10.0 uF), resistor R1 (500 Ohms), light emitting diode (LED), and time meter 32 (P/N T33BM733-DC from ENM Co.).

In use, pressure switch 24 is adjusted to close at a pressure level just below that of the CPAP pressure prescribed for the patient. When device 16 is turned on and mask 22 properly fitted, pressure at the prescribed level is delivered to the patient and also delivered by way of hose 26 to switch 24, which closes. In this way, hose 26 and switch 24 present an effective means for sensing the pressure at nasal mask 22, which is a parameter indicative of the status of usage of unit 12 by the patient. More particularly, pressure above the pressure switch setting indicates that the patient is using apparatus 10, and pressure below this setting indicates the status of non-usage.

With switch 24 closed, power at 12 VDC (supplied by device 16) is delivered to capacitor C1 and to the input of voltage regulator 30, which supplies a regulated output at +5 VDC to capacitors C2, C3, resistor R1, and meter 32. With this supply voltage, meter 32 is activated as is the LED by way of resistor R1. While activated, meter 32 records accumulated time.

If mask 22 becomes dislodged or not properly seated thereby presenting excessive leakage, the pressure inside mask 22 drops substantially below the set point pressure. When this occurs, switch 24 opens to de-energize timer circuit 28 and deactivate meter 32.

Figure 3:
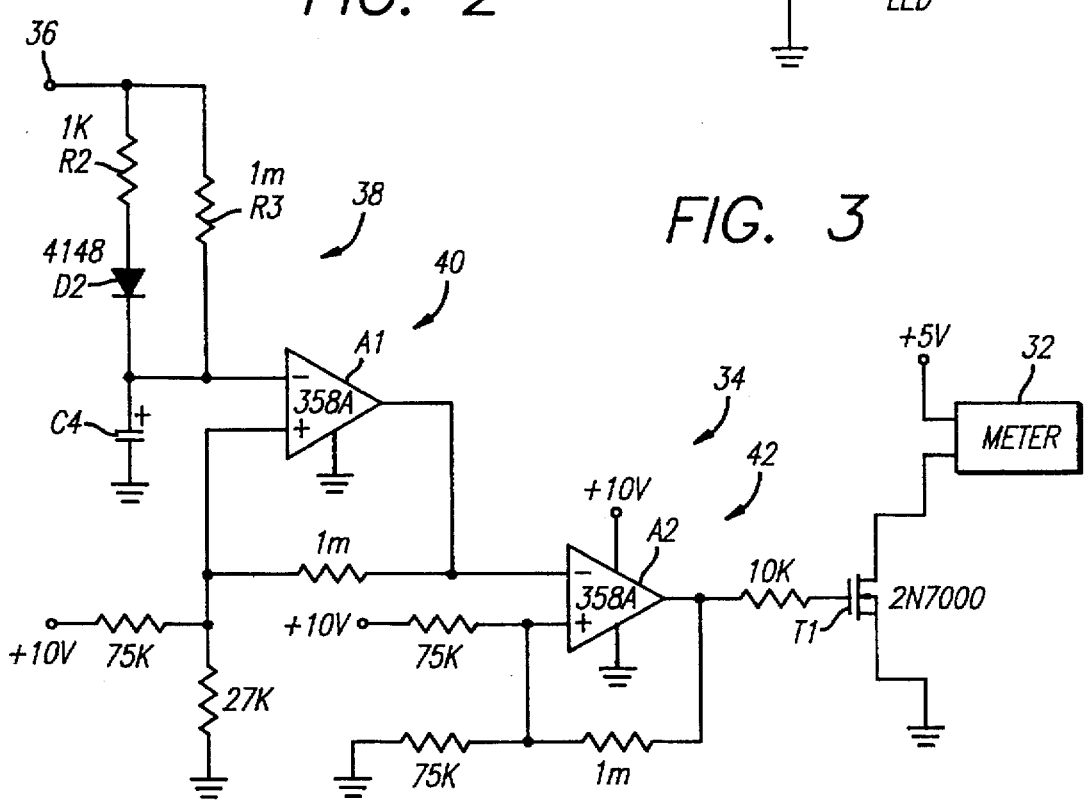
FIG. 3 is an electrical schematic of a second embodiment of the preferred compliance circuit.

FIG. 3 illustrates circuit 34 which is a second embodiment of the preferred compliance circuit. The input to this circuit is provided at terminal 36 and is preferably in form of logic signals such as a voltage at +9 VDC during exhalation of a patient and at 1.0 VDC during patient inhalation. Such an input can be provided, for example, by a conventional flow transducer placed in connection hose 20 with appropriate interface circuitry to provide the desired logic signals corresponding to patient exhalation and inhalation. With such an arrangement, air flow through hose 20 provides an indication of whether the patient is respirating, at least in part, through hose 20. The desired input signals could also be provided through other means responsive to patient respiration such as a pressure transducer in mask 22, a current monitor coupled with the blower motor of device 16, a heat sensor in the mask, or a position sensor coupled with a control valve that might be used to control the pressure delivered to the patient.

Circuit 34 includes network 38 composed of resistors R2 (1K), R3 (1M), diode D2 (type 4148) and capacitor C4, inverter network 40, inverter network 42, field effect transistor T1 and meter 32. Networks 40 and 42 include operational amplifiers A1 and A2 respectively interconnected with various resistors as shown in FIG. 3 so that these respective networks function as simple inverters.

In the operation of circuit 34, a logic high input at +9 VDC at terminal 36 corresponds to patient exhalation. This input rapidly charges capacitor C4 through resistor R2 and diode D2. Amplifier A1 inverts this signal to a logic low input to amplifier A2 which again inverts to provide a logic high output to the gate of transistor T1, which turns on and thereby activates meter 32.

When the input at terminal 36 goes low (+1 VDC) during patient inhalation, capacitor C4 discharges slowly through resistor R3. More particularly, the time constant of resistor R3 and capacitor C4 is about 10 seconds which maintains the logic high input to amplifier A1 during normal patient inhalation (lasting less than 10 seconds). The next patient exhalation results in recharging of capacitor C4. In this way, the operation of meter 32 is maintained during the entire respiratory cycle of the patient and thereby accurately accumulates the usage time of apparatus 10 by the patient.

If the patient removes mask 22, or excessive leaks develop, a subsequent exhalation signal is not provided at terminal 36 to recharge capacitor C4. After 10 seconds, the input voltage to amplifier A1 is sufficiently low so that a logic high output is provided to amplifier A2 which in turn provides a logic low output to the gate of transistor T1 which turns off and de-energizes meter 32.

As those skilled in the art will appreciate, the present invention encompasses many variations in the preferred embodiments described herein. For example, the invention finds utility in the context of CPAP, IPAP, and other pressure regimens. Additionally, a wide variety of inputs can be provided indicative of patient usage of the therapeutic apparatus so that the actual time of usage can be determined.

Having thus described the preferred embodiments of the present invention, the following is claimed as new and desired to be secured by Letters Patent:

1. A system for providing signals indicative of a patient's respiration, comprising:

a motor;

a monitor, said monitor operating to identify characteristics relating to current supplied to the motor;

a meter for tracking the identified characteristics;

means for communicating the identified characteristics to said meter; and means based upon the identified characteristics for providing signals indicative of a patient's respiration.

2. A system for providing signals indicative of a patient's respiration, comprising:

a mask for interfacing with a patient's respiratory system;

a heat sensor, said heat sensor operating to identify characteristics relating to temperatures in the mask;

a meter for tracking the identified characteristics;

means for communicating the identified characteristics to said meter; and means based upon the identified characteristics for providing signals indicative of a patient's respiration.

3. A system for providing signals indicative of a patient's respiration, comprising:

a control valve;

a position sensor, said position sensor operating to identify characteristics relating to positions assumed by the control valve;

a meter for tracking the identified characteristics;

means for communicating the identified characteristics to said meter; and means based upon the identified characteristics for providing signals indicative of a patient's respiration.

4. A system for providing signals indicative of a patient's respiration, comprising:

a mask for interfacing with a patient's respiratory system;

a pressure transducer, said pressure transducer operating to identify characteristics relating to pressures in said mask;

a meter for tracking the identified characteristics;

means for communicating the identified characteristics to said meter; and means based upon the identified characteristics for providing signals indicative of a patient's respiration.

* * * * *